United States Patent (10) Patent No.: US 9,408,759 B2
Sasayama et al. (45) Date of Patent: *Aug. 9, 2016

(54) DISPOSABLE DIAPER

(71) Applicant: UNICHARM CORPORATION, Shikokuchuo-shi, Ehime (JP)

(72) Inventors: Kenichi Sasayama, Kanonji (JP); Kunihiko Katsuragawa, Kanonji (JP)

(73) Assignee: UNICHARM CORPORATION, Ehime (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/403,742

(22) PCT Filed: Jun. 3, 2013

(86) PCT No.: PCT/JP2013/065403
§ 371 (c)(1),
(2) Date: Nov. 25, 2014

(87) PCT Pub. No.: WO2013/183603
PCT Pub. Date: Dec. 12, 2013

(65) Prior Publication Data
US 2015/0126953 A1 May 7, 2015

(30) Foreign Application Priority Data

Jun. 4, 2012 (JP) ................................. 2012-127462

(51) Int. Cl.
*A61F 13/15* (2006.01)
*A61F 13/49* (2006.01)
(52) U.S. Cl.
CPC ..... *A61F 13/49014* (2013.01); *A61F 13/49017* (2013.01); *A61F 13/49061* (2013.01)
(58) Field of Classification Search
CPC ................... A61F 13/49017; A61F 13/49092; A61F 13/49406; A61F 13/49413; A61F 13/49446; A61F 13/49453; A61F 13/64; A61F 13/49061; A61F 13/4906
See application file for complete search history.

(56) References Cited

U.S. PATENT DOCUMENTS 5,554,145 A 9/1996 Roe et al.
5,649,919 A 7/1997 Roessler et al.
(Continued)

FOREIGN PATENT DOCUMENTS

EP 1011582 A1 6/2000
EP 1827335 A1 9/2007
(Continued)

OTHER PUBLICATIONS

International Search Report mailed Aug. 27, 2013 in International Application No. PCT/JP2013/065403 filed Jun. 3, 2013.
Extended European Search Report in EP Application No. 13801014.5 dated Jan. 18, 2016.

*Primary Examiner* — Bradley Philips
(74) *Attorney, Agent, or Firm* — Hauptman Ham, LLP

(57) ABSTRACT

A disposable diaper includes a chassis, front and rear waist regions, and a crotch region between the front and rear waist regions and a liquid-absorbent structure extending at least in the crotch region. The chassis includes a pair of first leg elastics, and a pair of second leg elastics. The first leg elastics are arranged so as to be rectilinear in the longitudinal direction. The second leg elastics are arranged at a distance from the longitudinal axis as viewed in the transverse direction larger than a distance from the longitudinal axis at which the first leg elastics are arranged and have rectilinear portions extending in the longitudinal direct at least in a portion of the crotch region close to the front waist region and curved portions spaced apart outwardly from each other from the rear waist region side ends of the rectilinear portions.

7 Claims, 8 Drawing Sheets

(56) References Cited

U.S. PATENT DOCUMENTS

| | | | |
|---|---|---|---|
| 6,312,420 B1 | 11/2001 | Sasaki et al. | |
| 6,325,787 B1 | 12/2001 | Roe et al. | |
| 2001/0004689 A1* | 6/2001 | Otsubo | A61F 13/49017 604/385.19 |
| 2002/0128617 A1 | 9/2002 | Roe et al. | |
| 2004/0224132 A1 | 11/2004 | Roe et al. | |
| 2012/0271266 A1 | 10/2012 | Sasayama et al. | |
| 2013/0123735 A1 | 5/2013 | Ichikawa et al. | |
| 2015/0182388 A1* | 7/2015 | Katsuragawa | A61F 13/49014 604/385.29 |

FOREIGN PATENT DOCUMENTS

| | | |
|---|---|---|
| JP | 07-184947 A | 7/1995 |
| JP | 9-509350 A | 9/1997 |
| JP | 11-299828 A | 11/1999 |
| JP | 2001-137281 A | 5/2001 |
| JP | 2002-330994 A | 11/2002 |
| JP | 2011-139857 A | 7/2011 |
| JP | 2012-050634 A | 3/2012 |
| WO | 98/29080 A1 | 7/1998 |
| WO | 2006/068549 A1 | 6/2006 |
| WO | 2006/068549 A8 | 6/2006 |

* cited by examiner

DISPOSABLE DIAPER

RELATED APPLICATIONS

The present application is a National Phase of International Application Number PCT/JP2013/065403, filed Jun. 3, 2013, which claims priority to Japanese Application Number 2012-127462, filed Jun. 4, 2012.

TECHNICAL FIELD

The present invention relates to disposable diapers.

BACKGROUND

Conventionally, disposable diapers are known which include a skin-facing surface and a non-skin-facing surface, a front waist region, a rear waist region, a crotch region lying between the front and rear waist regions, first and second elastically contractile members extending in a longitudinal direction Such a disposable diaper is disclosed in JP H7-184947 A and further includes a liquid-impermeable sheet lying on the non-skin-facing surface side, a liquid-permeable sheet lying on the skin-facing surface side and an absorbent structure interposed between the liquid-permeable sheet and the liquid-impermeable sheet.

The liquid-permeable sheet is provided on the skin-facing surface side with a pair of lateral barrier sheets so as to be symmetrical to each other about the longitudinal axis. The first elastically contractile members are provided along inner lateral edges of the lateral barrier sheets extending close to the longitudinal axis with lateral barrier sheets so that the lateral barrier sheets may be spaced upwardly from the liquid-permeable sheet.

The first elastically contractile members are attached to sleeves defined by the inner lateral edges of the lateral barrier sheets lying close to the longitudinal axis folded inwardly and rectilinearly extend in the longitudinal direction.

The second elastically contractile members are interposed between the liquid-permeable sheet and the liquid-impermeable sheet along outer lateral edges at a distance from the longitudinal axis larger than a distance from the longitudinal axis at which the first elastically contractile members are arranged and rectilinearly extend in the longitudinal direction.

The liquid-permeable sheet in the rear waist region is provided on the skin-facing surface side with a waist barrier sheet adapted to connect a pair of the lateral barrier sheets. The waist barrier sheet is formed of, for example, urethane foam material and provided with third elastics extending in the transverse direction.

CITATION LIST

Patent Literature

{PTL 1}: JP H7-184947 A

SUMMARY

Technical Problem

In the diaper disclosed in JP H7-184947 A, the inner lateral edges of the paired lateral barrier sheets are pulled toward each other under the effect of the third elastics and, in consequence, there is a problem that the inner lateral edges of the lateral barrier sheets might dig into the wearer's posterior rugae.

An object of the present invention is to provide a disposable diaper adapted to prevent the sheets from digging into the wearer's posterior rugae.

Solution to Problem

To solve the problem set forth above, the present invention relates to a disposable diaper having a longitudinal direction, a transverse direction and a longitudinal axis extending in the longitudinal direction to bisect a dimension in the transverse direction, and including a chassis having a skin-facing surface and a non-skin-facing surface, a front waist region, a rear waist region, a crotch region lying between the front and rear waist regions and a liquid-absorbent structure extending in the longitudinal direction at least in the crotch region.

The diaper according to the present invention further includes the following features:

the chassis includes a first sheet, a second sheet and a pair of first leg elastics and a pair of second leg elastics both pairs being interposed between the first sheet and the second sheet so as to be symmetric about the longitudinal axis, a main portion and a pair of lateral elastic regions folded so as to face the main portion and attached to only front and rear ends in the longitudinal direction of the main portion. The first leg elastics and the second leg elastics are arranged in these lateral elastic regions; the first leg elastics are arranged so as to be relatively close to the longitudinal axis as viewed in the transverse direction; and the second leg elastics are arranged at a distance from the longitudinal axis as viewed in the transverse direction larger than a distance from the longitudinal axis at which the first leg elastics are arranged and have rectilinear portions extending in the longitudinal direction at least in a portion of the crotch region close to the front waist region and curved portions gradually spaced outwardly from each other at end portions of the rectilinear portions on the new waist region.

Advantageous Effects of Invention

In the disposable diaper according to the present invention, the first leg elastics are arranged so as to extend rectilinearly in the longitudinal direction and such an arrangement makes it possible to prevent the chassis from being spaced away from the wearer's skin in the crotch region. In addition, the second leg elastics are arranged at a distance from the longitudinal axis larger than a distance of the first leg elastics from the longitudinal axis and include the rectilinear portions at least in the portion of the crotch region close to the front waist region and the curved portions from the ends of the rectilinear portions on the rear waist region side and spaced outwardly from each other. Such unique arrangements ensure that undesirable separation of the chassis from the wearer's skin in the portion of the crotch region close to the front waist region, and a contractile force of the curved portions of the paired second leg elastics pulls the paired first leg elastics so as to draw apart the first leg elastics from each other. In this way, it is possible to prevent the first sheet and the second sheet from digging into the wearer's posterior rugae.

DESCRIPTION OF EMBODIMENTS

First Embodiment

Figure 1:
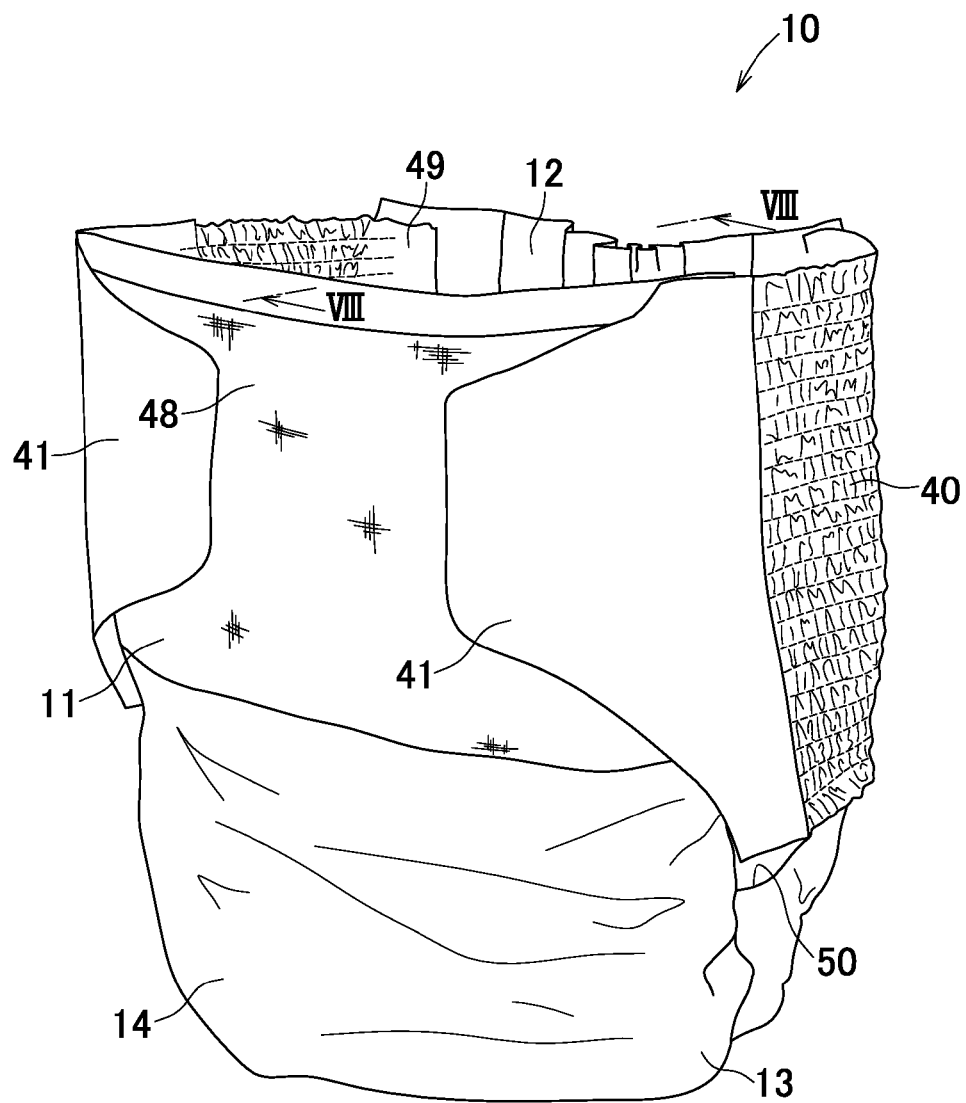
FIG. 1 is a perspective view of a disposable diaper according to a first embodiment of the present invention.
Figure 2:
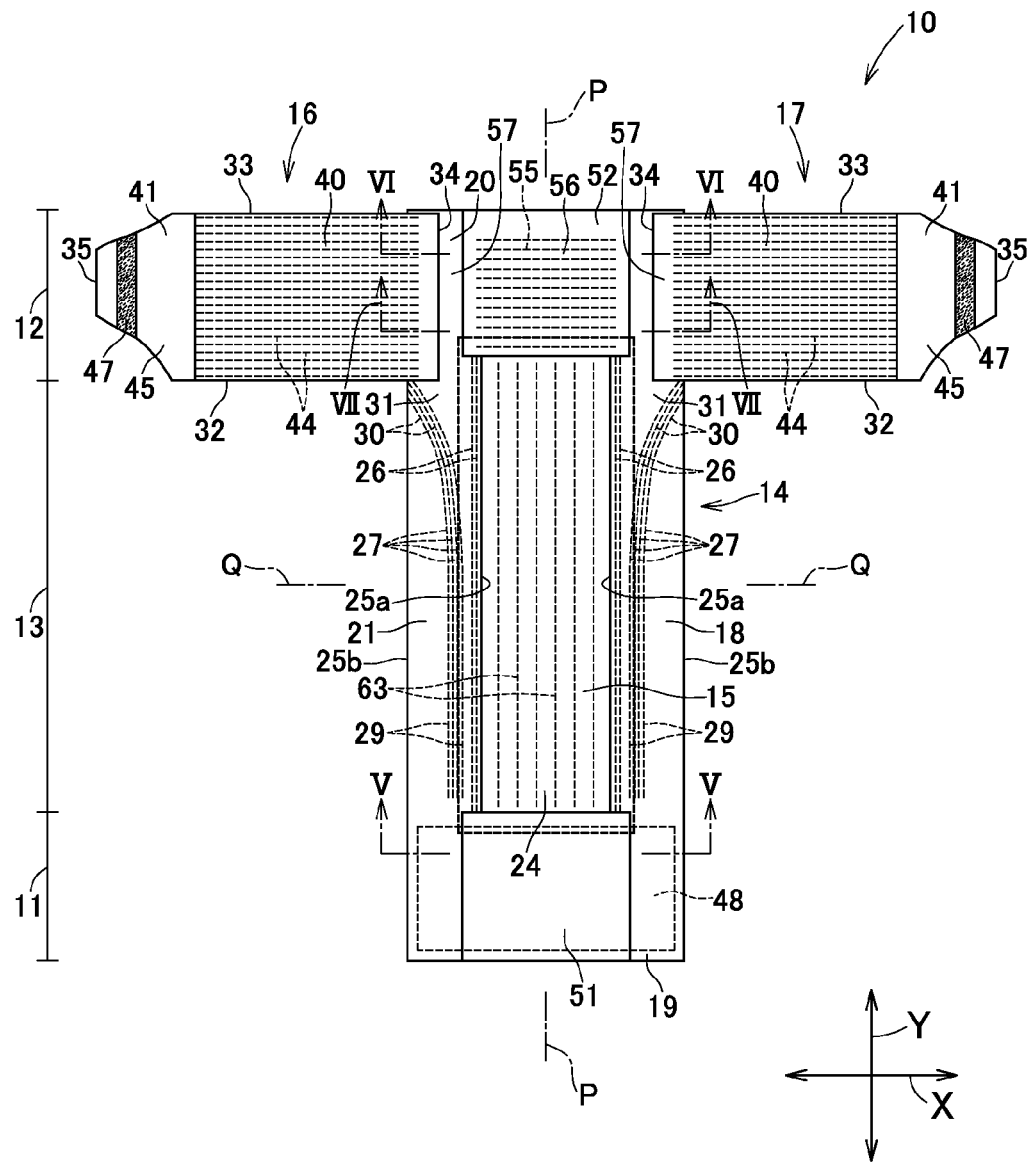
FIG. 2 is a developed plan view of the diaper developed in a front-back direction after respective associated mechanical fasteners have been disengaged from each other.
Figure 3:
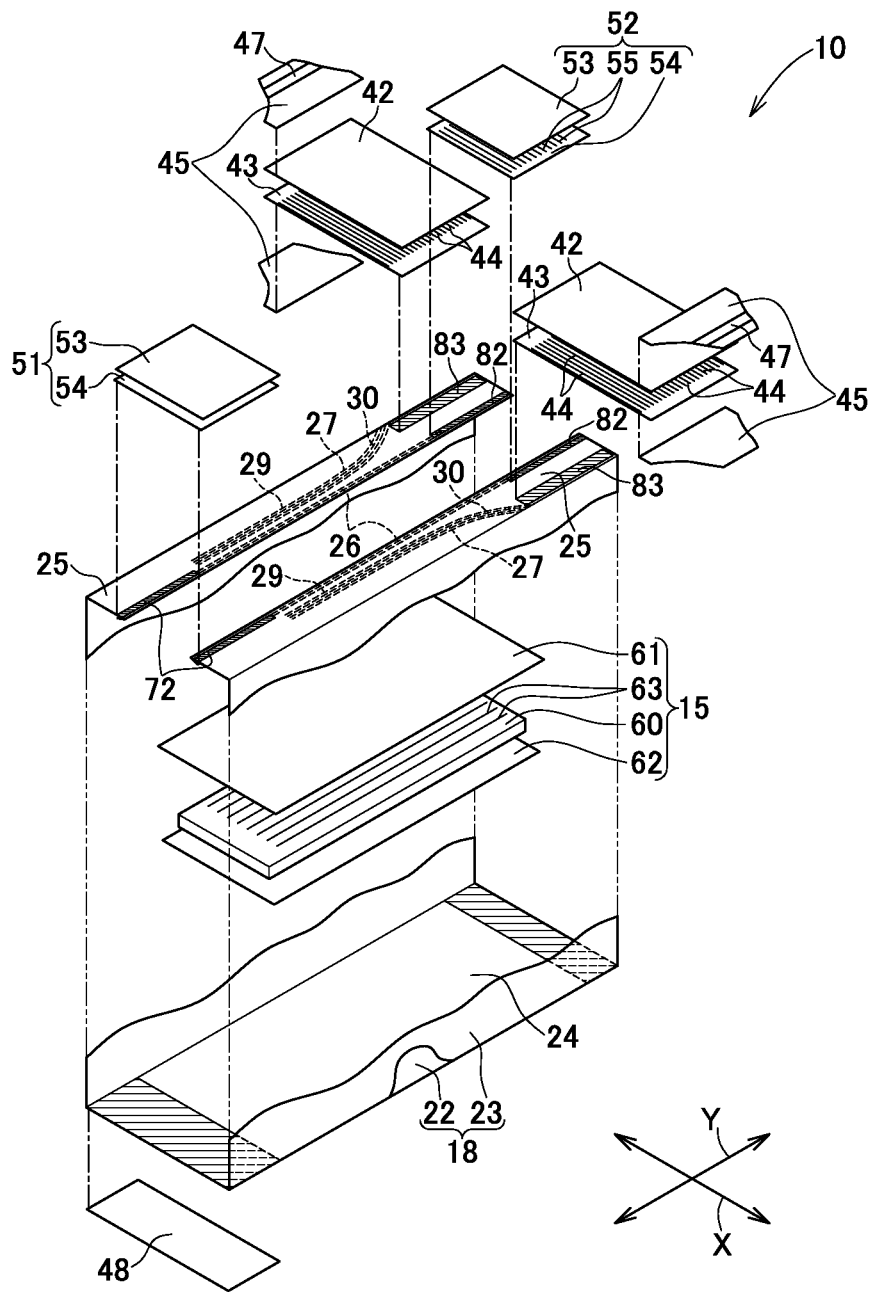
FIG. 3 is an exploded perspective view of the diaper.

Referring to FIGS. 1 through 4, an open-type disposable diaper 10 according to this embodiment has a longitudinal direction Y, a transverse direction X which is orthogonal to the longitudinal direction Y, a transverse axis Q-Q bisecting a dimension in the longitudinal direction Y of the diaper 10 and extending in the transverse direction X, a longitudinal axis P-P bisecting a dimension in the transverse direction X of the diaper 10 and extending in the longitudinal direction Y. The diaper 10 includes a chassis 14 having a skin-facing surface, a non-skin-facing surface, a front waist region 11, a rear waist region 12 and a crotch region 13 extending in the longitudinal direction Y between the front and rear waist regions 11, 12; a liquid-absorbent structure 15 attached to the skin-facing surface at least in the crotch region 13; and first and second elastic belt panels 16, 17 extending outwardly in the transverse direction X from lateral edges in the rear waist region 12 of the chassis 14.

The chassis 14 is longitudinally long, generally rectangular configuration and has a cover sheet 18, a front end portion 19 lying in the front waist region 11, a rear end portion 20 lying in the rear waist region 12 and an intermediate portion 21 lying in the crotch region 13. The outer cover 18 has first and second sheets 22, 23 each formed of a liquid-impermeable fibrous nonwoven fabric sheet, a plastic film or a laminate sheet composed thereof. These first and second sheets 22, 23 are joined to each other with a hot melt adhesive (not shown) distributed to an interior surface of one of these two sheets 22, 23. The chassis 14 includes a main portion 24 and a pair of lateral elastic regions 25 defined by folding opposite lateral portions of the outer cover 18 inwardly onto the main portion and joining the main portion 24. The lateral elastic regions 25 have inner lateral edges 25a and outer lateral edges 25b defined by folded regions of the outer cover 18.

The first sheet 22 is folded along the outer lateral edges 25b so as to lie on the skin-facing surface side in the main portion 24 and on the non-skin-facing surface side in the lateral elastic regions 25. The second sheet 23 lies on the non-skin-facing surface side in the main portion 24 and on the skin-facing surface side in the lateral elastic regions 25.

The respective lateral elastic regions 25 are provided with a plurality of thread, strand or string first leg elastics 26 and second leg elastics 27 and thereby elasticized at least in the longitudinal direction Y. The first leg elastics 26 rectilinearly extend in the longitudinal direction Y along the inner lateral edges 25a of the respective lateral elastic regions 25. In other words, the first leg elastics 26 are arranged closely to the longitudinal axis P-P as viewed in the transverse direction X.

The second leg elastics 27 lie outboard of the first leg elastics 26 as viewed in the transverse direction X and include rectilinear portions 29 extending from the transverse axis Q-Q toward the side of the front waist region 11 and curved portions 30 extending from the transverse axis Q-Q toward the side of the rear waist region 12. In other words, the second leg elastics 27 are arranged at a distance in the transverse direction X from the longitudinal axis P-P larger than a distance at which the first leg elastics 26 are arranged and include the rectilinear portions 29 extending in the longitudinal direction Y at least on the side of the crotch region 13 close to the front waist region 11 and the curved portions 30 gradually drawn apart from each other as the rectilinear portions 29 extend closer to the rear waist region 12.

On the side of the crotch region 13 close to the rear waist region 12, first non-contractile regions 31 which are directly unaffected by the contractile force of the first leg elastics 25 and the second leg elastics 27 are defined between the first leg elastics 26 and the second leg elastics 27.

The first and second leg elastics 26, 27 are secured between these sheets 22, 23 under tension in the longitudinal direction Y with a hot melt adhesive distributed to the inner surface of either of the first and second sheets 22, 23.

Each of the elastic belt panels 16, 17 has end edges 32, 33 spaced apart from and opposed to each other in the longitudinal direction Y and inner and outer lateral edges 34, 35 spaced apart from and opposed to each other in the transverse direction X. The inner lateral edges 34 rectilinearly extend in the longitudinal direction Y and the outer lateral edges 35 are convex outwardly in the transverse direction X. The inner lateral edges 34 of the respective elastic belt panels 16, 17 are attached in the vicinity of the outer lateral edges 25b of the respective lateral elastic regions 25 with an adhesive or by fusion-bonding, as will be described later. The elastic belt panels 16, 17 further include first elastic portions 40 which are stretchable in the transverse direction X and tabs 41 lying outboard of the associated first elastic portions 40 as viewed in the transverse direction X.

Each of the first elastic regions 40 includes a first belt sheet 42 formed of a fibrous nonwoven fabric or a plastic sheet and lying on the side of the skin-facing surface, a second belt sheet 43 lying on the side of the non-skin-facing surface and a plurality of thread, strand or string first waist elastics 44 extending in the transverse direction X so as to be spaced apart from each other in the longitudinal direction Y. The first waist elastics 44 are contractibly disposed between the first and second belt sheets 42, 43 under tension in the transverse direction X with a hot melt adhesive. The first waist elastics 44 are arranged so that the opposite ends of these elastics 44 are adjacent to the respective ends of the first leg elastics 26 lying on the opposite sides of the rear waist region 12.

Each of the tabs 41 is formed of generally trapezoidal sheet materials 45. The sheet materials 45 may be composed of, for example, fibrous nonwoven fabrics or plastic sheets. These two sheet materials are respectively joined to the first sheet 42 and the second sheet 43 with an adhesive or by fusion bonding and the outer side portion of the first elastic region 40 is secured between the sheet materials 45.

Outer end portions of the respective sheet materials 45 are provided on the skin-facing surfaces thereof with first fastening elements 47 each formed of sheet material having a relatively high stiffness and tensile strength such as, for example, a plastic film, a fibrous nonwoven fabric or a laminate thereof or craft paper and including a multiplicity of hooks of a mechanical fastener. Referring to FIG. 1, the front waist region 11 is provided on its entire exterior surface with a second fastening element 48 formed of sheet material having a relatively high stiffness and a tensile strength such as, for example, a plastic film, a fibrous nonwoven fabric, a laminate thereof or craft paper and including a multiplicity of loops of a mechanical fastener. The first fastening elements 47 may be detachably engaged with the second fastening element 48 to define a waist-opening 49 and a pair of leg-openings 50.

The second fastening element 48 is provided on the approximately entire outer surface of the front waist region 11 and a range to be targeted by the first fastening element 47 is sufficiently large, whereby the waist size of the diaper 10 is readily adjustable. While conventional open-type diapers are usually put on the wearer's body lying on the back, the diaper 10 according to the present invention may be relatively easily put on the wearer's body even when the wearer is in an upright posture. Specifically, a helper or a care person may hold the front waist region 11 against the wearer's entire abdominal region with the one hand and simultaneously put the first fastening elements 47 into engagement with the second fastening element 48 with the other hand.

Between the lateral elastic regions 25 in the front and rear waist regions 11, 12, waist pocket panels 51, 52 are disposed in the vicinity of the inner lateral edges 25a so as to cross the liquid-absorbent structure 15. Each of the waist pocket panels 51, 52 includes an interior sheet 53 formed of a liquid-impermeable SMS (spunbonded/meltblown/spunbonded) fibrous nonwoven fabric or a spun bonded nonwoven fabric having a mass per unit area in a range of about 5 to about 15 g/m$^2$ and an exterior sheet 54 formed of a breathable plastic sheet.

The waist pocket panel 52 lying in the rear waist region 12 additionally includes a plurality of thread, strand or string second waist elastics 55 interposed between the interior and exterior sheets 53, 54. The second waist elastics 55 extend in the transverse direction X and spaced apart from each other in the longitudinal direction Y. The second waist elastics 55 are contractibly disposed under tension between the interior and exterior sheets 53, 54 with a hot melt adhesive. The waist pocket panel 52 has a second elastic region 56 defined by the region in which the second waist elastics 55 are arranged and thereby elasticized at least in the transverse direction X. Of the second waist elastics 55, one or more elastics 55 lying relatively close to the transverse axis Q-Q are arranged to have respective opposite ends which are adjacent to the ends of the first leg elastics 26 lying on the side of the rear waist region 12.

The first and second leg elastics 26, 27 may be formed of thread, strand or string elastic material each having a fineness in a range of about 470 to about 940 dtex and a tensile ratio in a range of about 2.0 to about 2.8, the first waist elastics 44 may be formed of thread, strand or string elastic material each having a fineness in a range of about 470 to about 940 dtex and a tensile ratio in a range of about 2.5 to about 3.0, and the second waist elastics 55 may be formed of thread, strand or string elastic material each having a fineness in a range of about 470 to about 940 dtex and a tensile ratio in a range of about 2.0 to about 2.5. In the diaper 10 developed in the longitudinal direction Y and the transverse direction X, a dimension in the transverse direction X of the first waist elastics 44, i.e., a dimension in the transverse direction X of the respective first elastic regions 40 is larger than a dimension in the transverse direction X of the second waist elastics 55, i.e., a dimension in the transverse direction X of the first elastic region 56. Specifically, the former's dimension is in a range of about 190 to about 230 mm and the latter's dimension is in a range of about 120 to about 160 mm. The dimension in the transverse direction X of the respective first elastic regions 40 may be set to be larger than that of the dimension in the transverse direction X of the second elastic region 56 in this manner to improve the fit about the wearer's waist, thereby preventing the crotch region from being displaced during use of the diaper 10. A tensile strength per unit area (designated hereunder simply as "tensile stress") of the respective first elastic regions 40 is preferably higher than a tensile stress of the second elastic region 56. More specifically, based on test pieces each having a dimension of 25 mm in the longitudinal direction Y cut out from the respective regions, a tensile stress of the first elastic regions 40 at 80% of the maximum elongation is about 1.3 N and a tensile stress of the second elastic region 56 at 80% of the maximum elongation is about 1.0 N. Since the tensile stress of the second elastic region 56 is lower than the tensile stress of the respective first elastic regions 40, when the diaper 10 is put on the wearer's body and the first and second elastic regions 40, 56 are circumferentially stretched about the wearer's waist, the second elastic region 56 is stretched at a degree higher than a degree at which the first elastic regions 40 are stretched and, in consequence, the waist pocket panel 52 stably fits about the wearer's waist.

The rear waist region 12 has the elastic belt panels 16, 17 and second non-contractile regions 57 which are defined between the elastic belt panels 16, 17 and the waist pocket panel 52 and directly unaffected by the contractile force of the first waist elastics 44 and the second waist elastics 55. In this diaper 10, the first non-contractile regions 31 and the second non-contractile regions 57 are arranged so as to be contiguous to each other in the longitudinal direction Y.

Since the first and second elastic regions 40, 56 contract in the transverse direction X in the waist region 12, the front and rear waist regions 11, 12 stably fit about the wearer's waist in the state of joined to each other. In this regard, it is possible to form the elastic belt panels 16, 17 and the waist pocket panel 52 from an elastic composite sheet continuously extending in the transverse direction X. However, with the arrangement according to this embodiment such that the waist pocket panel 52 and the elastic belt panels 16, 17 are separately formed and the first elastic regions 40 and the second elastic region 56 are spaced apart from each other in the rear waist region 12, the first leg elastics 26 are pulled outwardly in the transverse direction X under contractile force of the elastic belt panels 16, 17 and the first leg elastics 26 should not be spaced away from the wearer's thighs during use of the diaper 10. In addition, with the arrangement such that the waist pocket panel 52 and the elastic belt panels 16, 17 are separately formed, it is possible to vary various conditions such as a distance dimension between the first waist elastics 44 and the second waist elastics 55 so that leakage of body exudates from the rear waist region 12 may be prevented under the contractile force of the first waist elastics 44 and an appropriate fit to the wearer's body may be ensured under the contractile force of the second waist elastics 55 and at the same time a desired air permeability is maintained through the elastic belt panels 16, 17. Additionally, since the second leg elastics 27 have curved portions 30 curving outwardly in the transverse direction X on the side of the rear waist region 12 so as to define the first non-contractile regions 31 and the second non-contractile regions 57 defined between the first leg elastics 26 and the second leg elastics 27 are contiguous to the first non-contractile regions 31 in the longitudinal direction Y. With such arrangement, the first non-contractile regions 31 inhibit contraction in the transverse direction X of the rear waist region 12 which would otherwise occur under the effect of the elastic belt panels 16, 17 and ensure that the rear waist region 12 is properly held in contact with the wearer's buttocks. Consequently, the rear waist region 12 and the portion of the crotch region 13 close to the rear waist region 12 should not dig into the posterior rugae. In addition, the elastic belt panels 16, 17 are located on both sides in the transverse direction X of these second non-contractile regions 57 so that the elastic belt panel 16 and the elastic belt panel 17 may be put on the wearer's body without biasing. As a result, the first non-contractile regions 31 may be properly located and whereby an undesirable displacement of the diaper 10 on the wearer's body may be inhibited.

The liquid-absorbent structure 15 is attached to the skin-facing surface of a main portion 24 of the outer cover 18 with a hot melt adhesive and includes a liquid-absorbent layer 60, a body side liner 61 formed of a liquid-permeable sheet and covering at least the skin-facing surface of the liquid-absorbent layer, and a leakage-barrier sheet 62 formed of a liquid-impermeable sheet and covering the non-skin-facing surface of the liquid-absorbent layer 60. Between the body side liner 61 and the liquid-absorbent layer 60, a plurality of thread, strand or string elastics 63 spaced apart from each other in the transverse direction X and extending in the longitudinal direction Y are arranged in a contractible state. Though not illustrated, the liquid-absorbent structure 15 is formed with a plurality of wrinkles/creases extending in the transverse direction X under contraction of the elastics 63. The elastics 63 arranged on the liquid-absorbent structure 15 facilitate the diaper 10 as a whole to be stretched in the longitudinal direction Y and, even for the wearer having a relatively large circumferential waist size and in a supine posture, the first fastening elements 47 may be easily engaged with the second fastening element 48.

The liquid-absorbent layer 60 is formed of an absorbent core including a mixture of superabsorbent polymer particles (SAP) which is water-insoluble and capable of absorbing an amount of water 10 times or more of its own mass, wood fluff pulp and optionally a small quantity of thermoplastic fibers and wrapped with a liquid-permeable sheet such as tissue paper and a hydrophilic nonwoven fabric.

Figure 4:
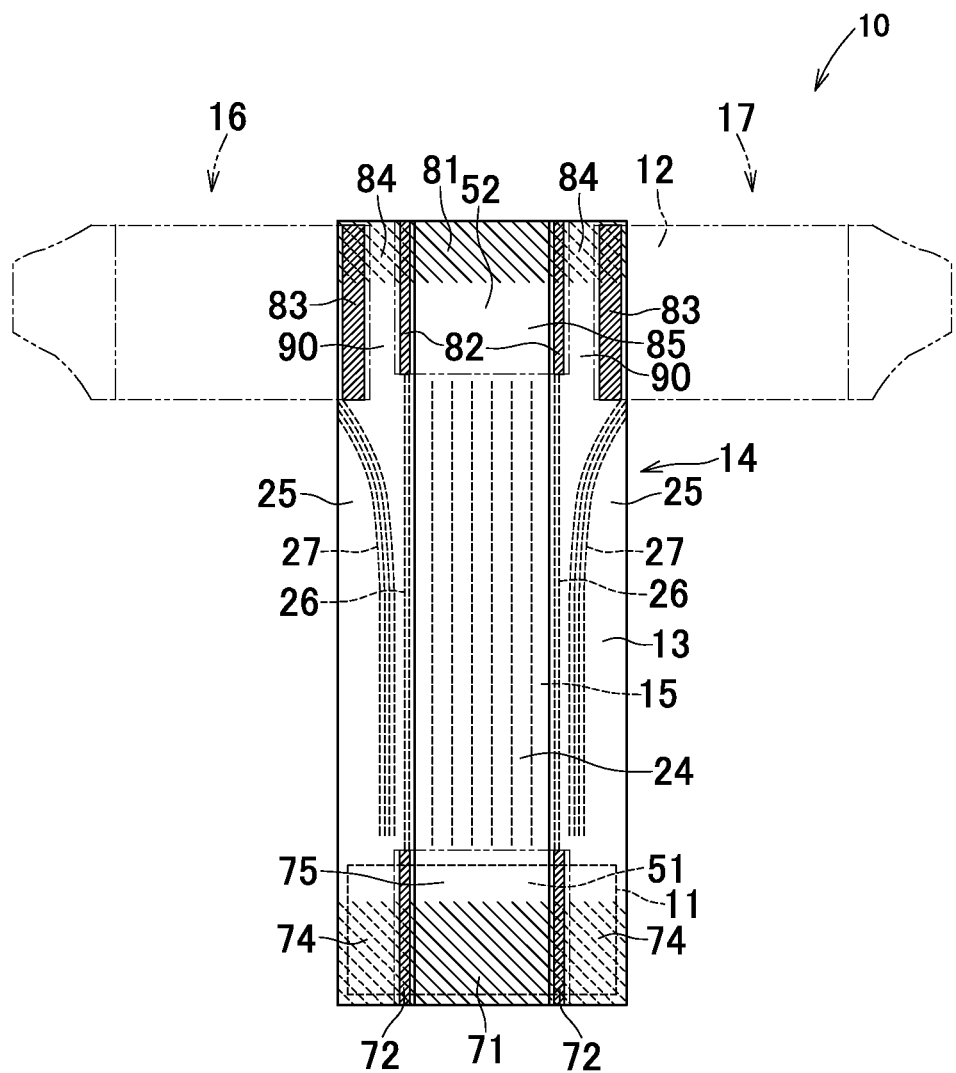
FIG. 4 is a developed plan view of the diaper, illustrating only respective joint regions with solid lines.
Figure 5:
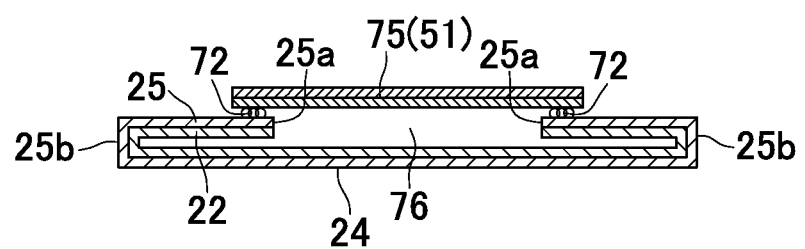
FIG. 5 is a schematic sectional view taken along line V-V in FIG. 2.

Referring to FIGS. 4 and 5, in the front waist region 11, a midsection in the transverse direction X of the waist pocket panel 51 is joined to the main portion 24 through a first joint region 71 extending in the transverse direction X on the skin-facing surface of the main portion 24 and the both lateral portions in the transverse direction X of the waist pocket panel 51 are joined to the lateral elastic regions 25 through second joint regions 72 extending in the longitudinal direction Y along the inner lateral edges 25a. Front end portions 74 of the respective lateral elastic regions 25 are joined to the main portion 24 through the first joint region 71. A dimension in the longitudinal direction Y of the first joint region 71 is smaller than a dimension in the longitudinal direction Y of the waist pocket panel 51 and a central non-joint region 75 in which the waist pocket panel 51 and the main portion 24 are not joined to each other is defined in a region surrounded by the first joint region 71 and the second joint regions 72 of the waist pocket panel 51. In this central non-joint region 75, a front space 76 adapted to receive body exudates is defined between the main portion 24 and the waist pocket panel 51. In other words, the waist pocket panel 51 is joined to the inner lateral edges 25a so that a front space 76 may be formed between the waist pocket panel 51 and the lateral elastic regions 25 and the main portion 24.

Figure 6:
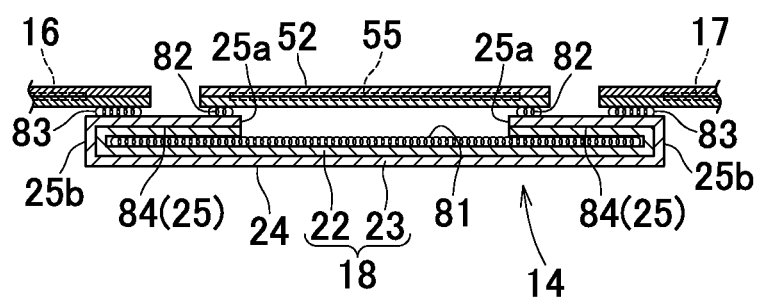
FIG. 6 is a schematic sectional view taken along line VI-VI in FIG. 2.
Figure 7:
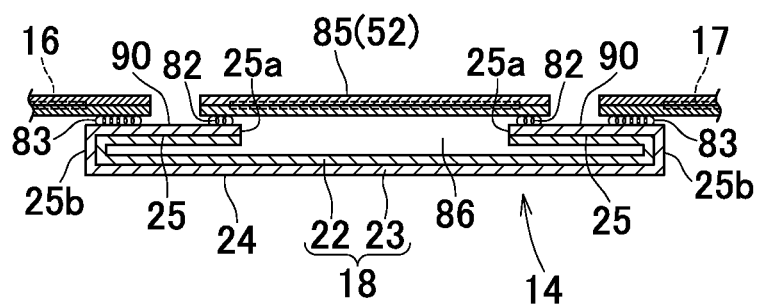
FIG. 7 is a schematic sectional view taken along line VII-VII in FIG. 2.

Referring to FIGS. 4, 6 and 7, in the rear waist region 12, a midsection in the transverse direction X of the waist pocket panel 52 is joined to the main portion 24 through a first joint region 81 extending in the transverse direction X on the skin-facing surface of the main portion 24 and the both lateral portions of the waist pocket panel 52 are joined to the lateral elastic regions 25 through second joint regions 82 extending in the longitudinal direction Y along the inner lateral edges 25a. Rear end portions 84 of the respective lateral elastic regions 25 are joined to the main portion 24 through the first joint region 81. A dimension in the longitudinal direction Y of the first joint region 81 is smaller than a dimension in the longitudinal direction Y of the waist pocket panel 52 and a central non-joint region 85 in which the waist pocket panel 52 and the main portion 24 are not joined to each other is defined in a region surrounded by the first joint region 81 and the second joint regions 82 of the waist pocket panel 52. In this central non-joint region 85, a rear space 86 adapted to receive body exudates is defined between the main portion 24 and the rear end portion of the liquid-absorbent structure 15 and the waist pocket panel 52. In other words, the waist pocket panel 52 is joined to the inner lateral edges 25a so that a rear space 86 adapted to receive body exudates may be formed between the waist pocket panel 51 and the lateral elastic regions 25 and the main portion 24.

In the rear waist region 12, the elastic belt panels 16, 17 are joined to the chassis 14 through third joint regions 83 extending in the longitudinal direction Y along the outer lateral edges 25b of the respective lateral elastic regions 25. The elastic belt panels 16, 17 are joined to the outer lateral edges 25b of the respective lateral elastic regions 25 and, consequently, during use of the diaper 10, the lateral elastic regions 25 are pulled in the transverse direction X under the effect of tensile strength of the elastic belt panels 16, 17 to put the inner lateral edges 25a in contact with the wearer's thighs, thereby forming leakage-barriers 87 to be described later. The lateral elastic regions 25 respectively include lateral non-joint regions 90 defined by the first joint region 81, the second joint regions 82 and the third joint regions 83, respectively. The elastic belt panels 16, 17 are attached to the skin-facing surface side of the main portion 24 along the outer lateral edges 25b and such arrangement prevents the main portion 24 from being directly pressed again the wearer's body and, in addition, facilitates a space for reception of body exudates to be formed between the main portion 24 and the waist pocket panel 52 during use of the diaper 10.

Figure 8:
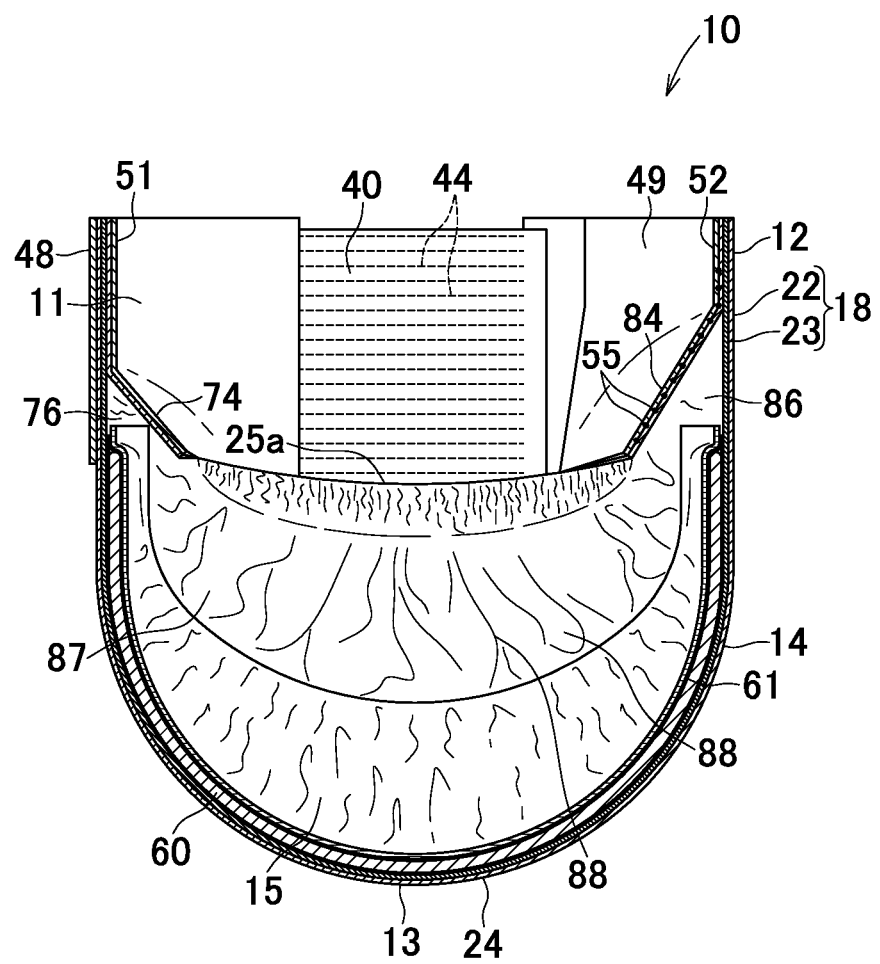
FIG. 8 is a schematic sectional view taken along line VIII-VIII in FIG. 1.

Referring to FIG. 8, during use of the diaper 10, the lateral elastic regions 25 are spaced apart from the liquid-absorbent structure 15 and the inner lateral edges 25a of the respective lateral elastic regions 25 come in contact with the wearer's thighs to form the leakage-barriers 87 so that the chassis 14 may have a U-configuration in cross-section. When body exudates is voided onto the liquid-absorbent structure 15 of the diaper 10 being put on the wearer's body, the liquid-absorbent structure 15 is spaced away from the wearer's buttocks under its own weight and a relatively large volumetric body exudates receiving space 88 is formed between the wearer's buttocks and the liquid-absorbent structure 15. Particularly in the front and rear waist regions 11, 12, the front and rear pockets 76, 86 are formed and, in addition, the lateral non-joint regions 90 are defined in the rear waist region 12. In this way, the further large volumetric body exudates receiving space 88 is ensured. Portions of the lateral elastic regions 25 lying in front of the rear end portions 84 of the respective lateral elastic regions 25 and adapted to rise up lie outboard of the inner end edges 32 of the elastic belt panels 16, 17 as viewed in the longitudinal direction Y. With such arrangements, when the diaper 10 is put on the wearer's body, the lateral elastic regions 25 are pulled up by the elastic belt panels 16, 17 to rise up to form the relatively large leakage-barriers 87 and allow further large amount of body exudates to be received. When a relatively large amount of body exudates is received and contained, the liquid-absorbent structure 15 is sufficiently spaced away from the wearer's buttocks and the wearer's buttocks should not be soiled with body exudates.

In this diaper 10, the first leg elastics 26 are arranged to extend rectilinearly in the longitudinal direction Y so as to prevent the chassis 14 from being spaced away from the wearer's skin in the crotch region 13. In addition, the second leg elastics 27 lie outboard of the first leg elastics 26 as viewed in the transverse direction X at a distance from the longitudinal axis P-P larger than a distance at which the first leg elastics 26 are arranged and include rectilinear portions 29 extending from the transverse axis Q-Q toward the side of the front waist region 11 and curved portions 30 extending from the transverse axis Q-Q toward the side of the rear waist region 12, and include the rectilinear portions 29 extending in the longitudinal direction Y at least on the portion of the crotch region 13 lying close to the front waist region 11 and the curved portions 30 gradually drawn apart from each other as the rectilinear portions 29 extend closer to the rear waist region 12. With such a unique arrangement, the chassis 14 should not be spaced away from the wearer's skin in the portion of the crotch region 13 lying close to the front waist region 11 and also a pair of the first leg elastics 26 may be pulled under the contractile force of the curved portions 30 of the second leg elastics 27 so that a pair of the first leg elastics may be spaced apart from each other. In this way, it is possible to prevent the first sheet 22 and the second sheet 23 from digging into the wearer's posterior rugae. Additionally, the first leg elastics 26 and the second leg elastics 27 are interposed between the first sheet 22 and the second sheet 23 and, in consequence, the contractile force of these elastics 26, 27 directly act on the first sheet 22 and the second sheet 23. As a result, it is possible to prevent further reliably the first sheet 22 and the second sheet 23 from digging into the wearer's posterior rugae.

Of the first waist elastics 44, ends of the elastics 44 lying relatively close to the transverse axis Q-Q are arranged to have ends which are adjacent to the ends of the second leg elastics 27 lying on the side of the rear waist region 12 so that an associated behavior of the contractile force of the first waist elastics 44 generated in the transverse direction X and contractile force of the second leg elastics 27 may be improved in the diaper 10 put on the wearer's body. Whereby the ends of the a pair of the second leg elastics 27 in the rear waist region 12 may be spaced apart from each other under the contractile force of the first waist elastics 44 prevent the first sheet 22 and the second sheet 23 from digging into the wearer's posterior rugae.

The diaper 10 further includes a pair of the lateral elastic regions 25 provided with the first leg elastics 26 and the second leg elastics 27, folded so as to face the main portion 24 and joined only at the front end portion 19 and the rear end portion 20 of the chassis 14. In the rear waist region 12, a pair of the elastic belt panels 16, 17 are attached to the outer lateral edges 25a of these paired lateral regions 25, and whereby an associated behavior of an associated behavior of the contractile force generated by the first waist elastics 44 attached to the elastic belt panels 16, 17 in the transverse direction X and contractile force generated by the second leg elastics 27 in the longitudinal direction may be improved in the diaper 10 put on the wearers body. In this way, the ends of the paired second leg elastics 27 in the rear waist region 12 may be spaced apart from each other under the effect of contractile force of the first waist elastics 44, thereby preventing the first sheet 22 and the second sheet 23 from digging into the wearer's posterior rugae.

The waist pocket panel 52 is located on the skin-facing surface side and, in consequence, the waist pocket panel 52 should not be spaced away from the wearer's skin in the rear waist region 12.

The contractile force of the second leg elastics 27 is higher than the contractile force of the second waist elastics 55 and the contractile force of the second waist elastics 55 may prevent the first sheet 22 and the second sheet 23 from digging into the wearer's posterior rugae.

Second Embodiment

Figure 9:
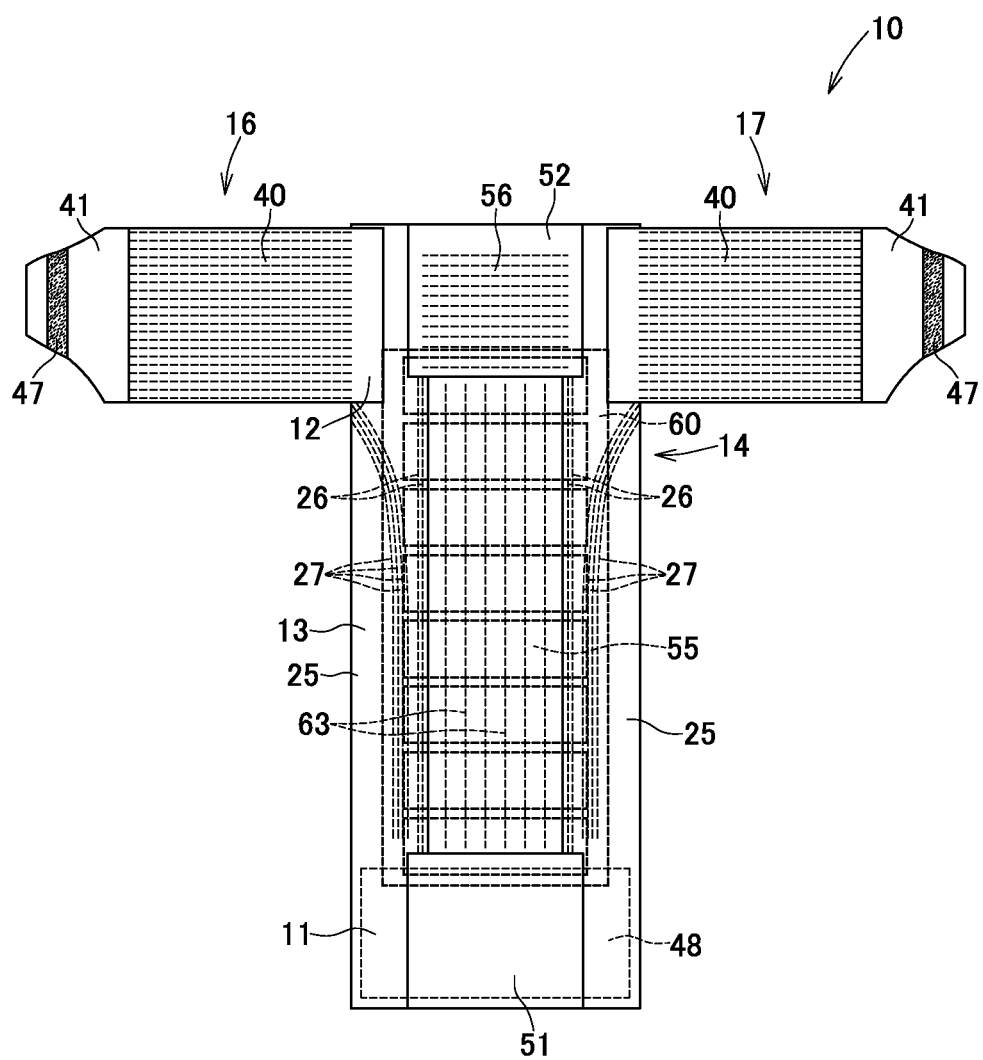
FIG. 9 is a developed plan view similar to FIG. 2, illustrating a second embodiment.
Figure 10:
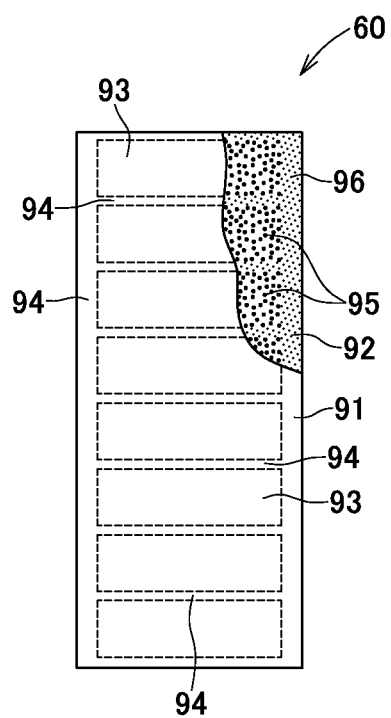
FIG. 10 is a partially cutaway developed plan view of the liquid absorbent structure of the second embodiment.

Referring to FIGS. 9 and 10, according to this embodiment, the liquid-absorbent layer 60 of the liquid-absorbent structure 15 includes absorbent materials composed primarily of superabsorbent polymer particles, a first belt sheet (upper sheet) 91 lying on the skin-facing surface and formed of a liquid-permeable fibrous nonwoven fabric having a mass per unit area in a range of about 8.0 to about 15.0 g/m$^2$, preferably a mass per unit area of 10.0 g/m$^2$ and a second sheet (lower sheet) 92 lying on the non-skin-facing surface and formed of a water-permeable or low-water-permeable SMS fibrous nonwoven fabric having a mass per unit area in a range of about 8.0 to about 15.0 g/m$^2$, preferably a mass per unit area of 11.0 g/m$^2$.

The liquid-absorbent layer 60 further includes a plurality of generally rectangular liquid-absorbent region 93 defined by cells spaced apart from each other by a given dimension in the longitudinal direction Y and a seal region 94 substantially not provided with the absorbent materials and surrounding the respective liquid-absorbent regions 93. In this regard, while the liquid-absorbent region 93 is divided into eight cells according to this embodiment, an area and the number of the cells of the liquid-absorbent region 93 may be appropriately varied depending on an absorption performance required for the liquid-absorbent structure 15 and, for example, the liquid-absorbent region 93 may be divided into eight or more cells or provided in the form of a single region extending over the entire liquid-absorbent structure 15.

In the liquid-absorbent region 93, superabsorbent polymer particles 95 having a mass per unit area in a range of about 30 to 300 g/m$^2$, preferably a mass per unit area in a range of about 40 to about 280 g/m$^2$ are generally evenly secured to the inner surface of the first sheet 91 with a hot melt adhesive 96. In order to adjust the absorption rate of the liquid-absorbent layer 60 as a whole, for example, two types of superabsorbent polymer particles having different absorption rates may be used together. So long as advantageous effects of the present invention may be ensured, the absorbent material may include, in addition to the superabsorbent polymer particles 95, various types of well known material such as fluff wood pulp and optionally thermoplastic fibers at a relatively low mixing rate. Specifically, when the water-absorbent fibers such as fluff wood pulp are mixed, preferably about 0 to about 30% by mass of the absorbent materials as a whole is mixed. While, as the hot melt adhesive 96, various types of well known adhesives may be used, a hydrophobic adhesive is preferably used to prevent the superabsorbent polymer particles from falling off the first belt sheet 91 after the body exudates have been absorbed.

In the liquid-absorbent region 93, the first sheet 91 and the second sheet 92 are preferably partially joined to each other or not joined to each other. When the first and second sheets, 91, 92 are partially joined to each other with the hot melt adhesive 96, it is possible to configure so that body exudates having moved into the liquid-absorbent layer 50 are absorbed by the superabsorbent polymer particles 95 and joining between the first and second sheets 91, 92 is released due to swelling of the superabsorbent polymer particles 95. Meanwhile, in the seal region 94, more specifically, boundary regions between respective pairs of the adjacent liquid-absorbent cells 93 and the entire peripheral region of the liquid-absorbent layer 60, the first and second sheets 91, 92 are joined to each other with the hot melt adhesive 96. In this regard, the hot melt adhesive 96 is distributed relatively densely, i.e., in a planar pattern in the liquid-absorbent region 93 in order to secure the superabsorbent polymer particles 95 to the inner surface of the first sheet 91, while in the seal region 94, the hot melt adhesive 96 is distributed relatively sparsely.

The absorbent materials of the liquid-absorbent layer 60 is composed of only the superabsorbent polymer particles 95 and the sheet member wrapping them as has described above and the absorbent materials are thinner than the case in which the absorbent materials are composed of a mixture of the superabsorbent polymer particles and fluff wood pulp. This means that the absorbent materials are flexible to conform to movements of the chassis. The first and second sheets 91, 92 are stably attached to each other in the seal region 94 to ensure a desired peel strength and a higher flexibility than the case in which the first and second sheets 91, 92 are joined to each other in whole area. In the liquid-absorbent region 93, the superabsorbent polymer particles 95 are evenly joined to the first sheet 91 and, in consequence, the superabsorbent polymer particles should not be unevenly distributed regardless of movement and posture of the wearer. While the seal region 94 is to seal the periphery of the liquid-absorbent region and thereby to prevent the movable superabsorbent polymer particles from falling off, a portion of the superabsorbent polymer particles 95 may sometimes creep into the seal region in the course of the manufacturing process in a range of mass per unit area smaller than a predetermined level. Though not illustrated, it is possible to arrange a plurality of elastics 63 extending in the longitudinal direction Y between the body side liner 61 and the liquid-absorbent layer 60 in a manner similar to the first embodiment.

The constituent elements of the diaper 10 are not limited to those described in the description but the other various types of material widely used in the relevant technical field may be used without limitation unless otherwise stated. The terms "first", "second" and "third" used in the description and Claims of the present invention are used merely to distinguish the similar elements, similar positions or the other similar means.

The disclosure of the present invention may be arranged in at least one or more of the following features.

A disposable diaper having a longitudinal direction, a transverse direction and a longitudinal axis extending in the longitudinal direction to bisect a dimension in the transverse direction, and including a chassis having a skin-facing surface and a non-skin-facing surface, a front waist region, a rear waist region, a crotch region lying between the front and rear waist regions and a liquid-absorbent structure extending in the longitudinal direction at least in the crotch region, wherein:
the chassis includes a first sheet, a second sheet and a pair of first leg elastics and a pair of second leg elastics both pairs being interposed between the first sheet and the second sheet so as to be symmetric about the longitudinal axis, a main portion and a pair of lateral elastic regions folded so as to face the main portion and attached to only front and rear ends in the longitudinal direction of the main portion wherein the first leg elastics and the second leg elastics are arranged in these lateral elastic regions;

the first leg elastics are arranged so as to be relatively close to the longitudinal axis as viewed in the transverse direction; and
the second leg elastics are arranged at a distance from the longitudinal axis as viewed in the transverse direction larger than a distance from the longitudinal axis at which the first leg elastics are arranged and have rectilinear portions extending in the longitudinal direction at least in a portion of the crotch region close to the front waist region and curved portions gradually spaced outwardly from each other in the rear waist region side ends of the rectilinear portions.

The invention claimed is:
1. A disposable diaper having a longitudinal direction and a transverse direction, and a longitudinal axis extending in the longitudinal direction to bisect a dimension in the transverse direction, the disposable diaper comprising:
a chassis including a skin-facing surface and a non-skin-facing surface, a front waist region, a rear waist region, a crotch region lying between the front and rear waist regions, and a liquid-absorbent structure extending in the longitudinal direction at least in the crotch region,
wherein
the chassis further includes
a first sheet,
a second sheet,
a pair of first leg elastics and a pair of second leg elastics, both said pairs being interposed between the first sheet and the second sheet so as to be symmetric about the longitudinal axis,
a main portion, and
a pair of lateral elastic regions folded so as to face the main portion and attached to only front and rear ends of the main portion in the longitudinal direction,
the first leg elastics and the second leg elastics are arranged in the lateral elastic regions,
the first leg elastics are arranged at a first distance from the longitudinal axis as viewed in the transverse direction,
the second leg elastics are arranged at a second distance from the longitudinal axis as viewed in the transverse direction, the second distance larger than the first distance,
the second leg elastics have
rectilinear portions extending in the longitudinal direction at least in a portion of the crotch region close to the front waist region, and
curved portions extending from the rectilinear portions toward the rear waist region and curved away from each other in the transverse direction,
a portion of the crotch region close to the rear waist region has first non-contractile regions respectively lying between the first leg elastics and the second leg elastics,
the rear waist region includes
a pair of elastic belt panels extending outwardly from lateral edges of the chassis in the transverse direction; and
a waist pocket panel through which inner lateral edges of the respective lateral elastic regions are connected to each other,
each of the elastic belt panels is provided with a plurality of first waist elastics spaced apart from each other in the longitudinal direction and extending in the transverse direction,
the waist pocket panel is provided with a plurality of second waist elastics spaced apart from each other in the longitudinal direction and extending in the transverse direction, the rear waist region has second non-contractile regions lying between the respective elastic belt panels and the waist pocket panel, and the first non-contractile regions and the second non-contractile regions are contiguous to each other in the longitudinal direction.

2. The diaper according to claim 1, wherein ends of the first waist elastics on a side toward the crotch region are adjacent to ends of the second leg elastics on a side toward the rear waist region.

3. The diaper according to claim 1, wherein the elastic belt panels are attached to outer lateral edges of the respective lateral elastic regions in the rear waist region.

4. The diaper according to claim 1, wherein the waist pocket panel lies on the skin-facing surface of the chassis; and ends of the second waist elastics in the transverse direction on a side toward the crotch region are adjacent to ends of the first leg elastics on a side of the rear waist region.

5. The diaper according to claim 1, wherein the inner lateral edges of the respective lateral elastic regions are connected to each other through the waist pocket panel to define a pocket between the waist pocket panel, the lateral elastic regions and the main portion.

6. The diaper according to claim 1, wherein the liquid-absorbent structure has a thickness direction being orthogonal to the longitudinal direction and the transverse direction and includes a liquid-permeable body side liner and a liquid-absorbent layer, and the waist pocket panel overlaps the liquid-permeable body side liner or the liquid-absorbent layer in the thickness direction.

7. The diaper according to claim 1, wherein a contractile force of the second leg elastics is higher than a contractile force of the second waist elastics.

* * * * *